United States Patent [19]

Morton et al.

[11] 4,107,287

[45] Aug. 15, 1978

[54] GC ANTIGEN-SPECIFIC IMMUNOCHEMICAL INDICATOR REAGENT AND METHOD FOR PREPARING SAME

[75] Inventors: Harry E. Morton, Drexel Hill; Gow T. Lam, Philadelphia, both of Pa.

[73] Assignee: University of Pennsylvania, Philadelphia, Pa.

[21] Appl. No.: 675,879

[22] Filed: Apr. 12, 1976

[51] Int. Cl.$^2$ .................... G01N 31/00; G01N 31/02; G01N 31/22; G01N 33/16

[52] U.S. Cl. .................................... 424/8; 23/230 B; 195/63; 195/103.5 A; 252/408; 424/3; 424/11; 424/12; 424/13

[58] Field of Search ...................... 424/3.8, 11, 12, 13; 23/230 B; 260/112 R, 112 B; 252/408; 195/4, 63, 103.5

[56] References Cited

U.S. PATENT DOCUMENTS

| | | | |
|---|---|---|---|
| 3,930,951 | 1/1976 | Messing | 195/63 |
| 3,983,000 | 9/1976 | Messing | 195/63 |

OTHER PUBLICATIONS

Prager, Fed. Proc., vol. 25, No. 2 P & I, Mar.-Apr. 1966, Ab. No. 337.
Borek, Nature, vol. 191, Sep. 1961, pp. 1293-1294.
Lam, Applied Microbiol., vol. 27, Feb. 1974, pp. 356-359.
Arrameas, Immunochemistry, vol. 6, 1969, pp. 67-76.

*Primary Examiner*—Albert T. Meyers
*Assistant Examiner*—A. P. Fagelson
*Attorney, Agent, or Firm*—Holman & Stern

[57] ABSTRACT

An immunochemical indicator reagent capable of indicating the presence of specific antigenic or haptenic material by hemagglutination reaction therewith, comprising the corresponding antibody globulin molecules chemically coupled to erythrocyte carrier particles through a bifunctional chlorine-terminated coupling agent consisting of either diazo blue B or diazo blue B-terminated condensation products of diazo blue B with glycine. The reagent is prepared by first treating the erythrocyte carrier particles with a proteolytic enzyme such as trypsin to provide the erythrocyte surface with additional exposed active hydrogen-containing groups including free amino groups, then fixing the erythrocyte carrier particles with a fixing agent, such as an aldehyde, and thereafter chemically coupling the erythrocyte carrier particles to the antibody globulin molecules by reaction with the bifunctional chlorine-terminated coupling agent. The coupling action of this coupling agent is preferentially through the free amino groups in each of the two materials being coupled, providing a chemical bond of high strength and stability, and further does not impair the antibody activity, resulting in the reagent having a high degree of sensitivity and stability. The indicator reagent may be used in performing hemagglutination tests directly with materials removed from animal bodies or with colonies of microorganisms or with tissue cells growing upon solid surfaces.

9 Claims, No Drawings

GC ANTIGEN-SPECIFIC IMMUNOCHEMICAL INDICATOR REAGENT AND METHOD FOR PREPARING SAME

BACKGROUND OF THE INVENTION

This invention relates to immunochemical indicator reagents and, more particularly, to such reagents capable of indicating the presence of specific antigenic or haptenic material by hemagglutination reaction therewith.

Agglutination testing and inhibition of agglutination testing are both well known techniques for indicating the presence of antibodies or antigens in a test specimen, such as a body fluid, secretion, exudate, transudate, tissue cells, a microorganism culture, or the like. Both of these techniques generally employ indicator reagents composed of a reactive moiety consisting of either antigens or antibodies, attached to suitable carrier particles for the purpose of providing the reagent with sufficient mass so that the product of the agglutination reaction may be readily detected with the unaided eye. In preparing such indicator reagents, the nature of the reactive moiety to be attached to the carrier particles will depend upon the type of material being detected, i.e., antibody or antigen, and the type of testing technique being employed, i.e., direct agglutination testing or inhibition of agglutination testing. For example, detection of specific antigenic material in a test specimen by direct agglutination testing would require an indicator reagent composed of carrier particles having attached thereto antibody globulin molecules having specific reactivity toward the specific antigenic material being detected, so that upon mixing the indicator reagent with the test specimen, the occurrence of an agglutination pattern would indicate the presence of the specific antigenic material being tested for, while the absence of an agglutination pattern would indicate the absence of that antigenic material.

Agglutination testing, being a relatively rapid, simple and economical procedure to perform, potentially has many advantages over other techniques currently commonly employed in clinical laboratories for the detection of specific antigenic material. Up to the present time, however, the technique of employing antibody-sensitized cells has not been widely employed for such purpose, due to the difficulties that have been encountered in preparing reliable indicator reagents having sufficient stability and sensitivity. The primary problem has been in obtaining an attachment of the antibody globulin molecules to the carrier particles which is sufficiently strong and stable so as to avoid leaching effect during storage or testing, without impairing the antigen-specific reactivity of the antibody globulin molecules. Thus, when attachment has been effected merely by physical adsorption of the antibody globulin molecules onto chemically inert carrier particles, such as quartz particles, bentonite particles, charcoal granules or latex particles, the antibody globulin molecules were found to leach from the surface of the carrier particles during storage in liquid suspension, freezing or lyophilization, as well as during the testing procedure itself, thereby leading to inaccurate test results. Moreover, previous attempts at using carrier particles having chemically reactive surface and effecting attachment of antibody globulin molecules thereto through chemical bonding have not produced bonds having a sufficiently high degree of strength and stability, and furthermore have generally resulted in an impairment of the antigen-specific reactivity of the antibody globulin molecules.

Of the chemically reactive carrier particles which have been proposed for this purpose, erythrocytes (red blood cells) are generally regarded as being the most suitable since they are readily available, their size is in the appropriate range to be detected in agglutination reactions by means of the unaided eye, their density is such that their rate of settling out of suspension produces agglutination reactions that can be read within a period of time that is practical (an hour or so), they are colored so their presence is easily detected, and their surface presents a large number and variety of chemical groups for possible reaction sites. In addition, the biconcave disc structure of erythrocytes and the extremely large number of plaques or raised areas on their surface further increase their effective surface area and provide the possibility of more chemically reactive sites being made available. Moreover, the one unsatisfactory feature of erythrocytes, their fragility, can be readily overcome by modifying the erythrocytes with some type of fixation, generally by treatment with an aldehyde fixing agent such as formaldehyde or glutaraldehyde.

The previous attempts at chemically bonding antibody globulin molecules to erythrocyte carrier particles have generally involved coupling reactions through the exposed aldehyde groups on the surface of aldehyde-fixed erythrocytes and exposed amino groups present in the antibody globulin molecules. Direct coupling of the two moieties in this manner has resulted in the antibody globulin molecules being bound too close to the surface of the erythrocyte carrier particles or falling into the crevices in the erythrocyte surface, leading to an impairment of the antigen-specific reactivity of the antibody globulin molecules due to steric hindrance effects. To avoid the steric hindrance effects, it has been found necessary to displace the antibody globulin molecules as far as possible from the surface of the erythrocyte carrier particles by means of a bifunctional coupling agent of substantial molecular size and having terminal reactivity with each of the two moieties being coupled. However, coupling agents meeting these requirements that have previously been tried for such purpose have not been found to be satisfactory due to their excessively high level of reactivity toward the antibody globulin molecules. For example, diazotized coupling agents, such as bis-diazotized benzidine and bis-diazotized dianisidine, which have been used with reasonable success in coupling antigens to erythrocyte carrier particles, have a destructive action toward antibody globulin molecules which impairs their antigen-specific reactivity, thereby resulting in indicator reagents having a relatively low degree of sensitivity. Moreover, the coupling action of these coupling agents to the erythrocyte surface, which is through the exposed aldehyde groups on the erythrocyte surface, results in chemical bonds whose degree of strength and stability is not exceptionally high and leaves substantial room for improvement.

SUMMARY OF THE INVENTION

It is accordingly a primary object of the present invention to provide an immunochemical indicator reagent capable of indicating the presence of specific antigenic or haptenic material by the hemagglutination reaction therewith, and having a high degree of sensitivity and stability.

Another object of the invention is to provide an immunochemical indicator reagent in accordance with the preceding object, which is capable of indicating the presence of specific antigenic or haptinic material by the hemagglutination reaction directly with body fluids or upon microorganisms or tissue cells growing upon or attached to solid surfaces.

A further object of the invention is to provide an immunochemical indicator reagent in accordance with the preceding objects, composed of antibody globulin molecules attached to erythrocyte carrier particles through chemical bonds having a high degree of strength and stability.

Still another object of the invention is to provide an immunochemical indicator reagent in accordance with the preceding objects, wherein the antigen-specific reactivity of the antibody globulin molecules is not impaired by its attachment to the erythrocyte carrier particles.

A still further object of the invention is to provide a method for chemically coupling antibody globulin molecules to erythrocyte carrier particles through a coupling agent of substantial molecular size which forms strong, stable chemical bonds with each of the two moieties being coupled without impairing the antigen-specific reactivity of the antibody molecules.

The above and other objects are achieved in accordance with the present invention by first treating erythrocyte carrier particles with a proteolytic enzyme capable of splitting some of the chemical bonds, particularly the peptide bonds, on the erythrocyte surface without destroying the erythrocyte integument, thereby providing the erythrocyte surface with additional exposed active hydrogen-containing groups including free amino groups. The enzyme-treated erythrocyte carrier particles are then fixed with an aldehyde fixing agent. Thereafter, antibody globulin molecules are chemically coupled to the fixed erythrocyte carrier particles through a bifunctional chlorine-terminated coupling agent selected from the group consisting of diazo blue B having the formula:

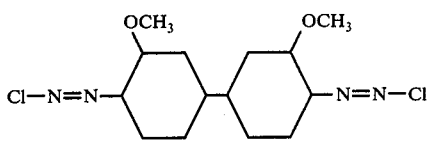

and diazo blue B-terminated condensation products of diazo blue B with glycine. The chemical coupling is effected by reaction of one chlorine-terminated end of the coupling agent predominantly with the free amino groups on the erythrocyte surface and reaction of the other chlorine-terminated end of the coupling agent predominantly with the free amino groups present on the surface of the antibody globulin molecules. Both of these coupling reactions result in the formation of chemical linkages which are quite strong and stable. Moreover, the coupling reaction has no observable destructive effect on the antibody activity of the globulin molecules and does not impair their antigen-specific reactivity. The resulting coupled product thus has a relatively high degree of stability and antigen-sensitivity, and may be used as an immunochemical indicator reagent in hemagglutination testing for indicating the presence of the specific antigenic or haptenic material toward which the antibody globulin molecules have specific reactivity.

DESCRIPTION OF PREFERRED EMBODIMENTS

The erythrocyte carrier particles for use in preparing the immunochemical indicator reagents of the present invention can be derived from a wide range of animal sources. Although sheep erythrocytes are generally preferred, erythrocytes derived from various other animals, such as rabbits, guinea pigs, rats, humans, goats, horses, chickens, and the like, also may be employed. The erythrocytes are collected in known manner by extracting a blood sample from an animal and then separating the erythrocytes from the serum by centrifugation. The erythrocytes are then recovered, washed, and suspended in isotonic saline solution prior to treatment in accordance with the present invention.

The characteristic structure of an erythrocyte is composed of an outer membrane which serves to contain a solution of hemoglobin. The outer membrane has a triple-layered structure of very complex chemical nature, including proteinaceous material made up of amino acids linked together through peptide bonds between the carboxyl group of one amino acid and the amino group of another amino acid. In order to render the erythrocytes suitable for use in the coupling reactions employed in preparing the indicator reagents in accordance with the present invention, the erythrocytes are first subjected to surface-modifying treatment with a proteolytic enzyme designed to increase the erythrocyte surface reactivity. The treatment with the proteolytic enzyme splits the peptide and other bonds of the proteinaceous material on the erythrocyte surface without destroying the integument of the erythrocyte, thereby providing the erythrocyte surface with increased exposed amino, carboxyl and other active hydrogen-containing groups and possibly liberating nonessential and interfering substances from the surface. As described in more detail hereinafter, the coupling action of the coupling agent employed in accordance with the present invention is preferentially, though not necessarily exclusively, through these exposed amino groups.

A proteolytic enzyme found to be satisfactory for modifying the erythrocyte surface in the above manner is trypsin. The conditioning of erythrocytes with trypsin is well known, and standardized trypsin preparations are readily commercially available, such as, for example, Bacto-Trypsin, 1:250 (Difco Laboratories, Inc., Detroit, Michigan). Treatment of erythrocytes with such standard trypsin preparations in a solution at pH 8.0 or slightly more alkaline, for example, at 37° C for approximately one hour or at room temperature for slightly longer periods, splits the peptide bonds of the proteinaceous material on the erythrocyte surface, without the erythrocytes losing their biconcave morphology or any significant amount of their hemoglobin. Other proteolytic enzymes capable of splitting the peptide bonds on the erythrocyte surface without destroying the erythrocyte substructure may be used in place of trypsin, such as, for example, pepsin, papain, pronase, ficin, chymotrypsin, bromelin, and mexacain.

The enzyme-treated erythrocyte carrier particles are then fixed in known manner by treatment with an aldehyde fixing agent. Fixation is that process by which the appearance of tissues or cells is preserved as they were when they were taken from the body for examination or use. The fixing agent penetrates into the interior of the cells and acts by coagulating the cell proteins and thereby hardens the cells. Fixation of the erythrocytes enables the erythrocytes to withstand further handling and stabilizes them against lysis or leakage of the hemoglobin out of the cells. Lysed erythrocytes would no longer be readily recognizable, would be lighter in weight and would not work well in the hemagglutination test.

The preferred aldehyde fixing agent is glutaraldehyde since it provides the best results in terms of enabling the erythrocytes to withstand freezing and not settling as rapidly or clumping as readily upon storage. Other aldehyde fixing agents that can suitably be employed include formaldehyde, malonaldehyde, succinaldehyde, pyruvic aldehyde, acrolein, methacrolein, and crotonaldehyde. The treatment with the aldehyde fixing agent may suitably be carried out, for example, in a 1 to 2% by volume aqueous solution of the aldehyde, preferably chilled in an ice bath. Following this treatment the fixed erythrocytes are washed with water to remove excess aldehyde. The fixation process does not interfere with the exposed amino and other active hydrogen-containing groups which were present or were exposed on the erythrocyte surface by means of the enzyme treatment, so that such exposed amino groups will still be present on the surface of the fixed erythrocytes.

The antibody globulin molecules which can be coupled to the fixed erythrocyte carrier particles in preparing the immunochemical indicator reagents in accordance with the present invention, can be any of the antibody globulin molecules produced in any animal. All antibody globulin molecules from a given species of animal are believed to be chemically similar since they are gamma globulin molecules modified in such a way that they have at two positions antigenic receptor sites for the antigenic material for which they are immunological counterparts. Hence, the main surface of antibody globulin molecules consists of roughly the same proteinaceous groups which are present in normal gamma globulin molecules, and contains exposed reactive amino and other active hydrogen-containing groups.

Immune globulins, those globulins capable of reacting with antigenic or haptenic material, are proteins of essentially the same composition as the normal globulins of the same animal species. However, due to the template effect of the antigen during the formation of the immune globulins, or antibody globulins, the sequence of the amino acids in the proteins or the coiling of the peptide chains in the globulin molecules are altered in the immune globulins so the immune globulins are capable of reacting with their specific antigens. The immune globulins produced against antigens of widely different nature, such as mycoplasma cells, bacterial cells and tissue cells, may have different chemical groups or different numbers of a given chemical group exposed at their surface and, therefore, some slight chemical modifications, which will be readily apparent to those skilled in the art, may have to be made to the surface of a particular immune globulin to compensate for the slight differences in the various types of immune globulins.

Such antibody globulin molecules are produced in various animals by injecting them with the corresponding antigenic material, and then isolating and recovering the resulting antibody globulin molecules in known manner from the immune sera of the animal. Exemplary of such antibody-producing antigenic materials are serum albumins, myoglobins, hemoglobins, ovalbumins, serum alpha, beta and gamma globulins, beta-lipoproteins, blood group substances A and B, human transferrins; hormones such as insulin and human chorionic gonadotropin (HCG); enzymes such as diastase, maltase, zymase, amylase and invertase; tissue cells and antigenic materials of either pathological or natural organisms exemplified by trichinella antigen, tuberculin purified protein derivatives, toxins and toxoids such as those of diphtheria and tetanus, mycoplasmas, gonococcus, meningococcus, pneumococcus, staphylococci, streptococci, rickettsia, viruses and the like.

The diazo blue B used as a coupling agent in preparing the immunochemical indicator reagents in accordance with the present invention, is a known compound and is readily available commercially, for example, from Sigma Chemical Co., St. Louis, Missouri, or INC Life Sciences Group, Cleveland, Ohio. Diazo blue B is the chlorine-terminated stabilized form of tetrazotized diorthoanisidine, and has the formula:

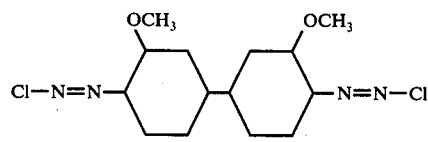

When diazo blue B is mixed in molar excess with an aqueous glycine solution, e.g., glycine-buffered saline solution, these materials will react to form diazo blue B-terminated condensation products of diazo blue B with glycine, such reaction proceeding at room temperature. Either diazo blue B itself or such diazo blue B-terminated condensation products of diazo blue B with glycine, can be used as the coupling agent in accordance with the present invention.

The presence of the terminal chlorine atoms provides these coupling agents with a high degree of reactivity toward active hydrogen-containing groups, particularly free amino groups, to the extent that reaction of the fixed enzyme-treated erythrocyte carrier particles prepared as described above with such coupling agents proceeds preferentially through the exposed free amino groups on the erythrocyte surface rather than through the exposed aldehyde groups or carboxyl groups. Although some reaction may possibly occur through these latter groups present on the erythrocyte surface, it would be minor in comparison with the reaction through the free amino groups. Such high degree of amino group-reactivity is not possessed by the non-chlorine-terminated coupling agents previously proposed, such as the unstabilized form of bis-diazotized dianisidine or bis-diazotized benzidine. The reaction between the free amino groups on the erythrocyte surface and one of the chlorine-terminated ends of the coupling agent results in that end of the coupling agent becoming covalently bound to the erythrocyte surface through a chemical linkage which has a much higher degree of strength and stability in comparison with the corresponding linkages formed through aldehyde or carboxyl groups.

The above-described bifunctional chlorine-terminated coupling agents likewise have a high degree of reactivity toward the free amino groups present on the surface of the antibody globulin molecules, and reaction of these amino groups with the other chlorine-terminated end of the coupling agent likewise results in a chemical linkage of high strength and stability covalently binding the antibody globulin molecules to such other end of the coupling agent. Moreover, while providing a strong and stable bond between the coupling agent and the antibody globulin molecules, such coupling reaction has a sufficiently mild effect toward the antibody globulin molecules so as not to impair their antigen-specific reactive sites, thereby enabling the production of antigen-specific indicator reagents having a high degree of sensitivity.

It is possible to utilize the coupling reactions described above for coupling the antibody globulin molecules to the fixed enzyme-treated erythrocyte carrier particles in preparing the indicator reagents in accordance with the present invention, merely by mixing the bifunctional chlorine-terminated coupling agent with an aqueous suspension of the two moieties to be coupled, and allowing the coupling reactions to proceed at room temperature. However, the better and the preferred procedure is to first react the erythrocyte carrier particles with a solution of diazo blue B in buffered saline, for example, by mixing for three hours at room temperature; separately reacting the antibody globulin molecules with a solution of diazo blue B in buffered saline, for example, by mixing at room temperature for one hour; and thereafter mixing the two reaction mixtures together and allowing reaction to proceed, for example, at room temperature over night. In a preferred embodiment of this procedure, the buffered saline contains glycine in an amount sufficient to conjugate a plurality of molecules of diazo blue B, resulting in the coupling agent being constituted of diazo blue B-terminated condensation products of diazo blue B with glycine. The longer spacer chain thus provided between the erythrocyte surface and the antigen-combining sites on the antibody globulin molecules further reduces the possibility of any steric hindrance effects, and furthermore permits more sites to participate and more antibody globulin molecules to be attached to an individual erythrocyte, thereby providing the final indicator reagent with greater sensitivity.

The above-described coupling procedure provides a strong and stable attachment of the antibody globulin molecules to the erythrocyte carrier particles and results in indicator reagents having a high degree of stability and sensitivity. Suspensions of these indicator reagents in buffered saline, preferably containing a protective colloid such as 1% normal rabbit serum, may be used in the conventional manner in hemagglutination testing to indicate the presence of the specific antigenic or haptenic material toward which the particular antibody globulin molecules have specific reactivity. For example, they can be used to identify directly by the agglutination reaction on colonies of mycoplasma or other microorganisms growing or grown on appropriate culture medium, or can be employed to detect the presence of specific antigens, particulate or in solution, in body fluids or other liquids, and are capable of detecting soluble antigenic material in the nanogram range. Such suspensions will retain their antibody activity for three to four weeks when stored in a refrigerator at 4° C, and furthermore are capable of being lyophilized and reconstituted as needed.

The invention is further illustrated by way of the following examples.

EXAMPLE 1

(a) Erythrocytes recovered from defibrinated sheep blood obtained commercially were washed three times with 0.15 M NaCl, and were then suspended in a standardized trypsin preparation solution, pH 8.0, and maintained therein at 37° C for one hour. The trypsinized erythrocytes were centrifuged, washed with 0.15 M NaCl, chilled in an ice bath, and then fixed in a chilled (in an ice bath) 1 to 2% (vol/vol) glutaraldehyde (25% solution, election microscope grade) solution containing one volume of 0.15 M phosphate buffer, pH 8.2, nine volumes of 0.15 M NaCl, and five volumes of deionized water. The cells were added slowly drop by drop from a pipette to the chilled fixing solution with vigorous stirring, the volume of glutaraldehyde solution used being sufficient to make a 1-2% cell suspension. The cell suspension was kept in the ice bath for thirty minutes and then placed at 4° C for another thirty minutes with occasional mixing throughout the fixation period. The fixed cells were centrifuged and washed with ten changes of 0.15 M NaCl and finally suspended in a sufficient volume of 0.11 M phosphate buffer, pH 7.3, or isotonic saline to give a 30% cell suspension. Merthiolate was added to a final concentration of 1:10,000 (wt/vol) as a preservative, and the suspension of glutaraldehyde-fixed trypsinized erythrocytes was stored at 4° C until ready for further use.

(b) A portion, 0.35 ml packed volume, of the above-prepared glutaraldehyde-fixed trypsinized erythrocyte suspension was washed twice with saline, and the cells were then suspended in a solution of 20 mg diazo blue B in glycine-buffered saline, pH 8.2, and allowed to react for three hours at room temperature with frequent mixing. At the end of the reaction period the suspension of treated cells was centrifuged, the supernate discarded, the packed cells washed once with said glycine-buffered saline, and resuspended in said glycine-buffered saline.

A solution containing 28 mg globulin fraction of anti-Mycoplasma arthritidis immune rabbit sera, isolated by means of ammonium sulfate precipitation, was mixed with a solution containing 2 mg diazo blue B in glycine-buffered saline, pH 8.2, and allowed to react for one hour at room temperature. This reaction mixture was then mixed with the erythrocyte-diazo blue B suspension in glycine-buffered saline resulting from the procedure described in the preceding paragraph, and incubated at room temperature for 30 minutes. Then a solution containing 5.35 mg of the same antibody globulin and a solution containing 1 mg diazo blue B were added, and the resulting reaction mixture was held at room temperature over night. The next day, the reaction mixture was incubated at 37° C for two hours, and then centrifuged. The globulin-sensitized cells were washed with glycine-buffered saline, pH 8.2, and resuspended in phosphate-buffered saline, pH 6.4, containing 1% normal rabbit serum and 0.1% Tween 80 to give a 0.5% suspension of the antibody-sensitized erythrocytes.

(c) The above-prepared antibody-sensitized erythrocyte suspension was utilized as an indicator reagent in direct agglutination testing to indicate the presence of *M. arthritidis*. When the indicator reagent suspension was added to colonies of *M. arthritidis* growing on the surface of solid media, an agglutination pattern that was easily detected with the unaided eye developed within one hour. Cross reactions were not observed with six heterologous species of mycoplasmas, and, in fact, the antibody-sensitized erythrocytes were actually repelled from colonies of such mucoplasmas at the beginning of the reaction period. The indicator reagent detected as little as 9 ng protein nitrogen in 0.025 ml of a soluble freeze-thaw extract of *M. arthritidis* by the hemagglutination reaction employing the microtiter technique.

EXAMPLE 2

Utilizing another portion of the glutaraldehyde-fixed trypsinized erythrocyte suspension prepared in accordance with Example (1a) the procedure of Example (1b) was repeated, but substituting anti-Mycoplasma hominis immune rabbit immune serum for the anti-Mycoplasma arthritidis immune rabbit sera. This antibody-sensitized erythrocyte suspension was utilized as an indicator reagent in direct agglutination testing to indicate the presence of *M. hominis*. When the indicator reagent suspension was added to colonies of *M. hominis* growing on the surface of solid media, an agglutination pattern on the surface of the colonies, which was easily detected with the unaided eye, developed within one hour. Cross reactions were not observed with six heterologous species of mycoplasmas, and, in fact, the antibody-sensitized erythrocytes were actually repelled from colonies of such heterologous types at the beginning of the reaction period.

EXAMPLE 3

Utilizing a portion of glutaraldehyde-fixed trypsinized erythrocyte suspension prepared in accordance with Example (1a), the procedure of Example (1b) was repeated, but substituting antigonococcal antibodies for the anti-Mycoplasma arthritidis antibodies. The resulting antibody-sensitized erythrocyte suspension was used as an indicator reagent in hemagglutination testing by the microtiter technique with a sample of urethral discharge from a male patient with suspected gonorrhea. An agglutination pattern which was easily detected with the unaided eye developed in one hour on the V-shaped bottom of the wells in the microtiter plate, providing a positive diagnosis of the presence of the gonococcus in the urethral discharge with an estimated as few as 11 gonococcal cells in the test as determined by appropriate culturing method. In comparison, the routine diagnostic laboratory required four days to isolate and identify the gonococcus by the recognized appropriate routine culturing procedures.

The test has been performed repeatedly with urethral secretions from men and cervical secretions from women each suspected of possibly harboring the gonococcus. In many cases the hemagglutination test was positive when gonococci were also demonstrated to be present by the usual culturing method. In some instances the hemagglutination test and the culturing method both gave negative reactions which gave the best evidence that the individuals were not infected with the gonococcus although on epidemiological evidence such individuals may have been exposed to the infection. Frequently the hemagglutination test was positive and the culture method failed to detect gonococci in patients who were diagnozed clinically of having gonorrhea. One of the advantages of the hemagglutination test is that it will give a positive reaction with gonococci, either living or dead or with their soluble products whereas only viable gonococci can give a positive reaction in the culturing procedures and in some instances the gonococci die during the interval between the removal of the specimen from the patient and depositing it on appropriate culture medium and placing it in an incubator. Also it is known that the best culture medium recommended for growing gonococci from clinical specimens will not grow gonococci in all cases from such specimens. In rare instances in individuals with a history of prior infection with gonococci and supposedly adequately treated for their infection upon recurrence of symptoms the hemagglutination test has been positive but the culture method failed to detect gonococci.

EXAMPLE 4

Utilizing a portion of another lot of glutaraldehyde-fixed trypsinized erythrocyte suspension prepared in accordance with Example (1a) the procedure of Example (1b) was repeated but substituting anti-HeLa cell rabbit immune serum for the anti-Mycoplasma arthritidis immune rabbit sera. This antibody-sensitized erythrocyte suspension was utilized as an indicator reagent in direct agglutination testing to indicate the presence of HeLa cells (human cancer cells) growing on glass cover slips.

While the primary utility of the indicator reagents of the present invention is in their capability of indicating the presence of specific antigenic or haptenic material by direct agglutination testing, it will be understood that the same indicator reagents can also be used for detecting the presence of the antibody itself in a fluid sample by inhibition of agglutination testing. For example, when testing for the presence of an antibody, a quantity of the antigen thereto can be added to the test medium prior to the addition of the indicator reagent of the present invention. If the fluid sample contains the antibody, the antigen added to the testing medium will preferentially react with this antibody and the antigen will thus be unable to agglutinate with the indicator reagent. Hence, the absence of an agglutination pattern would indicate the presence of the antibody being tested for, while the occurrence of an agglutination pattern would indicate the absence of that antibody. This is the well known hemagglutination inhibition reaction or HAI test.

The embodiments of the invention in which an exclusive property or privilege is claimed are defined as follows:

1. An immunochemical indicator reagent capable of indicating the presence of specific antigenic or haptenic material by hemagglutination reaction therewith, comprising a first moiety consisting of fixed enzyme-treated erythrocyte carrier particles whose surfaces are provided with exposed active hydrogen-containing groups including free amino groups, and a second moiety consisting of antibody globulin molecules having specific reactivity toward said specific antigenic or haptenic material and also having exposed active hydrogen-containing groups including free amino groups, said first and second moieties being chemically coupled together through a bifunctional chlorine-terminated coupling agent selected from the group consisting of diazo blue B having the formula

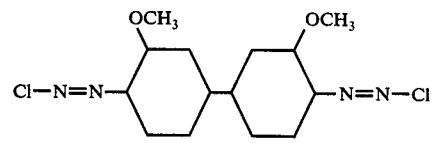

and diazo blue B-terminated condensation products of diazo blue B with glycine, each of said first and second moieties being covalently bound to opposite ends of said coupling agent predominantly through chemical linkages formed by reaction between the respective chlorine-terminated ends of said coupling agent and the free amino groups of the respective moieties.

2. The immunochemical indicator reagent of claim 1, wherein said first moiety consists of glutaraldehyde-fixed trypsinized erythrocyte carrier particles.

3. The immunochemical indicator reagent of claim 2, wherein said coupling agent consists of diazo blue B-terminated condensation products of diazo blue B with glycine.

4. A method for the preparation of an immunochemical indicator reagent capable of indicating the presence of specific antigenic or haptenic material by hemagglutination reaction therewith, comprising the steps of:
(a) treating erythrocyte carrier particles with a proteolytic enzyme capable of splitting the peptide bonds on the erythrocyte surface without destroying the erythrocyte integument, thereby providing the erythrocyte surface with additional exposed active hydrogen-containing groups including free amino groups;
(b) fixing the enzyme-treated erythrocyte carrier particles with an aldehyde fixing agent; and
(c) chemically coupling the fixed erythrocyte carrier particles to antibody globulin molecules having specific reactivity toward said specific antigenic or haptenic material and also having exposed active hydrogen-containing groups including free amino groups, said chemical coupling being effected through a bifunctional chlorine-terminated coupling agent selected from the group consisting of diazo blue B having the formula

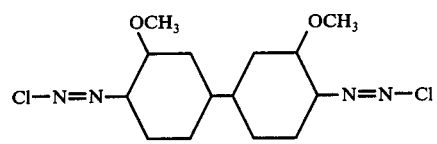

and diazo blue B-terminated condensation products of diazo blue B with glycine by reaction of one chlorine-terminated end of said coupling agent predominantly with said free amino groups on the erythrocyte surface and reaction of the other chlorine-terminated end of said coupling agent predominantly with said free amino groups in said antibody globulin molecules.

5. The method of claim 4, wherein said proteolytic enzyme is trypsin.

6. The method of claim 4, wherein said aldehyde fixing agent is glutaraldehyde.

7. The method of claim 4, wherein said chemical coupling is effected by reacting said fixed erythrocyte carrier particles with diazo blue B to form a first reaction mixture, reacting said antibody globulin molecules with diazo blue B to form a second reaction mixture, and thereafter reacting together said first and second reaction mixtures.

8. The method of claim 7, wherein said chemical coupling reactions are carried out in buffered saline solution.

9. The method of claim 8, wherein said buffered saline solution contains glycine in an amount sufficient to conjugate a plurality of molecules of diazo blue B, whereby said coupling agent is constituted of diazo blue B-terminated condensation products of diazo blue B with glycine.

* * * * *